United States Patent
Elsner et al.

(10) Patent No.: US 7,986,997 B2
(45) Date of Patent: Jul. 26, 2011

(54) COMMUNICATION MODULE AND METHOD OF OPERATION THEREOF

(75) Inventors: Joachim Elsner, Berlin (DE); Bernhard Gromotka, Berlin (DE); Martin Lang, Weisendorf (DE); Julian Merlin, Berlin (DE)

(73) Assignee: Biotronik CRM Patent AG (CH)

( * ) Notice: Subject to any disclaimer, the term of this patent is extended or adjusted under 35 U.S.C. 154(b) by 271 days.

(21) Appl. No.: 11/219,538

(22) Filed: Sep. 2, 2005

(65) Prior Publication Data
US 2006/0052843 A1 Mar. 9, 2006

(30) Foreign Application Priority Data
Sep. 3, 2004 (DE) .................. 10 2004 043 212

(51) Int. Cl.
*A61N 1/08* (2006.01)
(52) U.S. Cl. ........................................... 607/60
(58) Field of Classification Search .............. 607/16, 607/32, 59, 60
See application file for complete search history.

(56) References Cited

U.S. PATENT DOCUMENTS

| | | | |
|---|---|---|---|
| 5,752,976 | A | 5/1998 | Duffin et al. |
| 6,427,088 | B1 * | 7/2002 | Bowman et al. ............... 607/60 |
| 6,553,262 | B1 | 4/2003 | Lang et al. |
| 6,893,395 | B1 * | 5/2005 | Kraus et al. .................. 600/300 |
| 7,110,823 | B2 * | 9/2006 | Whitehurst et al. ........... 607/60 |
| 2003/0114898 | A1 * | 6/2003 | Von Arx et al. ............... 607/60 |

FOREIGN PATENT DOCUMENTS

| | | |
|---|---|---|
| DE | 195 02 654 | 8/1996 |
| DE | 195 19 450 | 11/1996 |
| DE | 696 03 858 | 1/2000 |
| DE | 198 51 135 | 5/2000 |
| DE | 198 19 127 | 10/2000 |
| DE | 102 13 114 | 10/2003 |
| DE | 698 11 649 | 11/2003 |
| WO | WO 97/25699 | 7/1997 |

* cited by examiner

*Primary Examiner* — Scott M Getzow
*Assistant Examiner* — Amanda Patton
(74) *Attorney, Agent, or Firm* — Hahn Loeser & Parks LLP

(57) ABSTRACT

A method of making a wireless communication connection between a patient device and an electromedical implant as communication partners is disclosed, wherein a transmitting unit of the patient device is continually switched on and off, so that the transmitting unit is alternately in an activity phase and an activity pause and during its activity pause at least once sends a recognition signal and wherein a receiving unit of the electromedical implant is continually switched on and off so that the receiving unit is alternately in an activity phase and an activity pause and during its activity phase checks whether the transmitting unit is just then in its activity phase and sends a recognition signal, wherein switching on and off of the receiving unit is so effected that an activity phase and an activity pause of the receiving unit together give an overall duration which differs from the overall duration of an activity phase and an activity pause of the transmitting unit so that within a foreseeable period of time the activity phases of the transmitting unit and the receiving unit overlap and a wireless communication connection between the two communication partners occurs.

16 Claims, 2 Drawing Sheets

COMMUNICATION MODULE AND METHOD OF OPERATION THEREOF

CROSS-REFERENCE TO RELATED APPLICATIONS/INCORPORATION BY REFERENCE

This U.S. patent application claims priority to German patent application 10 2004 043 212.0 filed Sep. 3, 2004.

TECHNICAL FIELD

Certain embodiments of the present invention relate to a method of temporal matching of the activity phases of a patient device and an electromedical implant as communication partners. Also, certain other embodiments of the present invention relate to an electromedical implant and a patient device comprising a receiving unit or a transmitting unit or both, a timer and a control unit, wherein the control unit periodically switches the receiving unit or the transmitting unit on and off after predetermined times measured by the timer.

BACKGROUND OF THE INVENTION

Communication partners which are respectively in transmitting and receiving communication with each other only for a short time and the methods of operating them are known in the state of the art in particular where a small available transmitting band width has to be distributed to a large number of transmitters and receivers. As there is not just any amount of transmitting band width available, the communication subscribers must manage therewith efficiently. Thus national and international standards for given permitted frequency bands prescribe the so-called listen-before-transmit method (LBT), in accordance with which any communication subscriber wishing to transmit in the specified frequency band must firstly observe the transmitting traffic present before that subscriber himself may transmit, after a prescribed period of time in which there is no radio traffic in the frequency band. Usually in that case one communication subscriber remains in the receiving mode and waits for a recognition signal from the communication partner, which signals the readiness to receive a mutual communication.

Modern electromedical implants, in particular cardiac pacemakers defibrillators and the like, offer physician and patients a very high degree of security and comfort by what is referred to as home monitoring functions.

In that respect the implant protocols diagnosis and therapy information and transmits that information to a portable external patient device by way of a telemetry interface. From there the data are passed to the home monitoring service center where they are stored and displayed for the physician. In that way the physician can be informed directly about therapy progress and the current state of health of his patients. He thus enjoys the possibility of reacting quickly to changes in the state of health of his patients.

Without home monitoring the physician can obtain those items of information only in the context of an examination of the patient. In critical situations that results in unwanted delays in the flow of information. In addition any examination involves a considerable amount of time for the patient and the physician. Frequent examinations result in a restriction in terms of mobility and quality of life, in particular for the patient.

With home monitoring, the implant information is sent by way of the described technical apparatus (see also U.S. Pat. Nos. 6,553,262 and 5,752,976) in the background without the patient being limited in terms of leading a normal life; in other words, he has the security of physician home monitoring without the stress caused by frequent examinations.

Indirect communication between an implant and a home monitoring service center is necessary for the reason that the implant can transmit only over a short distance once again by virtue of the strict demands in respect of power consumption. The short distance between the patient device and the electromedical implant also ensures that the transmission signal of the patient device, in spite of screening by the body of the patient, is sufficiently strong to be received by the implant.

In the case of such an electromedical implant which is disposed in the body of a patient however, the difficulty which arises is that the implant is screened by the surrounding body so that weak signals which just occupy the transmission channel cannot be perceived. The electromedical implant could thus wrongly view the transmission channel as being unused, claim it for itself and interfere with the communication of other devices. An LBT protocol cannot therefore be initiated by an electromedical implant, and for that reason a communication must always be initiated by the external patient device which is in a position to listen to the transmission channel with the necessary level of sensitivity.

Uninterrupted reception readiness on the part of the receiver also means an additional current requirement which is unacceptably high under some circumstances, for a battery-operated communication device. That applies in particular to electromedical implants such as for example a cardiac pacemaker which is placed in the body of a patient ready for operation over a number of years without the possibility of charging up or replacing the batteries. In the case of electromedical implants it would therefore be advantageous to be able also to continually switch off the receiver and to switch it on again only at the moments of the expected transmission on the part of the communication partner.

In order to guarantee the patient a freedom of movement which is as unrestricted as possible, the patient device in the form of a portable unit usually communicates with the home monitoring service center by way of a wireless data or telephone connection. As the operation of cellular radio devices is prohibited at numerous locations such as for example in hospitals or aircraft, a patient can be obliged to temporarily switch off the patient device.

A problem now however is that, after the patient device is switched on, the moment of the next reception cycle of the cardiac pacemaker is not known and the two devices therefore must provide for temporal matching to each other of their activity phases. That can also happen if the radio channel was in the meantime occupied by an outside device so that the cardiac pacemaker and the patient device could not communicate with each other. The above-indicated limitations in regard to use of the permitted frequency bands in question however impose tight limits as the receiving unit of the cardiac pacemaker cannot be continually switched on even after loss of contact with the patient device.

Further limitations and disadvantages of conventional, traditional, and proposed approaches will become apparent to one of skill in the art, through comparison of such systems and methods with the present invention as set forth in the remainder of the present application with reference to the drawings.

SUMMARY OF THE INVENTION

In accordance with an embodiment of the present invention, a method of temporal matching of the activity phases of a transmitter and a receiver which are respectively only active for a short time is provided.

In accordance with an embodiment of the present invention, a patient device and a cardiac pacemaker which are adapted to make and maintain a communication connection, wherein both communication partners are active only periodically for a short time, is provided.

In accordance with an embodiment of a method of the present invention, the transmitting and receiving units of the two communication modules are switched on and off in such a way that the operating periods resulting from activity phase and activity pause are of different lengths for the two communication partners. In that way, the relative temporal position of the two activity phases of the communication partners is continually displaced relative to each other so that, after a predetermined maximum time, there is an overlap of the two activity phases.

Advantageously, the method is carried out in such a way that the activity phase of the transmitting unit of the transmitting patient device is of the same length as the activity phase of the receiving electromedical implant.

Particularly, rapid overlap of the activity phases of the two communication partners which are not temporally matched to each other can be achieved if the operating period of one of the communication partners is selected to be longer or shorter respectively by the duration of an activity phase of the other communication partner.

In order to minimize the power consumption of the first receiving unit of the electromedical implant, the duration of the activity pause of the first receiving unit is, in accordance with an embodiment of the present invention, greater than the duration of the activity pause of the first transmitting unit.

In accordance with a particular variant embodiment of the method, the duration of an operating period, in relation to the duration of the activity phase contained in the operating period, is not an integral multiple of the corresponding operating period of the other communication partner in relation to the duration of the activity phase thereof. In that way, in the course of time, the activity phases of the two communication partners are displaced relative to each other so that superimposition thereof occurs within a given maximum time. That would not be guaranteed if the operating periods relative to each other were integral multiples.

If the activity phases of the transmitting and receiving units of the two communication partners overlap, the receiving communication partner can particularly easily determine the most favorable moment of its next activity phase if the transmitting communication partner transmits the beginning of its next activity phase as a difference in relation to the moment of the current transmission operation. In a particularly advantageous variant embodiment of the method according to the present invention, therefore, the patient device transmits the moment of its next activity phase as a difference in relation to the moment of the current transmission operation.

In accordance with an embodiment of the present invention, after reception of a signal communicating the moment of the beginning of the next activity phase of the first transmitting unit of the patient device, the electromedical implant switches off the first transmitting unit until the communicated moment, in order to save energy.

So that the receiving unit of the electromedical implant is, if possible, switched on only when the patient device is actually active after a first overlap of the activity phases of the transmitting and receiving units, a particular variant embodiment of the method provides for adaptation of the duration of the activity phase and the activity pause of the electromedical implant to the duration of the activity phase and the activity pause of the patient device.

If the communication connection between the electromedical implant and the patient device has collapsed again after synchronization has occurred, for example because the transmission channel was occupied or the patient device was switched off, the activity phases and pauses of the two communication partners are matched to each other again. For that purpose, in accordance with a variant embodiment of the method according to the present invention, the electromedical implant, after adaptation has occurred, shortens or lengthens the duration of the activity pause of the first transmitting unit again if the electromedical implant has received no recognition signal from the patient device during an activity phase of the first receiving unit.

In accordance with an embodiment of the present invention, the electromedical implant transmits an acknowledgement signal by way of a second transmitting unit as soon as the activity phases of the two communication modules are overlapping so that the patient device, after reception of the acknowledgement signal, can build up a periodically continued communication connection with the receiving communication module.

In a further variant embodiment of the method, the patient device, after reception of the acknowledgement signal, adapts the duration of its activity phase and activity pause to those of the electromedical implant. That alternative method also guarantees maximum overlap of the activity phases of the two communication modules after a first overlap of the activity phases has occurred.

If, after synchronization has taken place, during an activity phase, the patient device does not receive an acknowledgement signal then, in accordance with a variant embodiment of the method according to the present invention, the patient device shortens or lengthens the duration of the activity pause of the first transmitting unit in order again to achieve synchronization of the activity phases and pauses of the two communication partners.

In accordance with an embodiment of the present invention, an electromedical implant is provided comprising a first receiving unit, a first timer and a first control unit, wherein the control unit is adapted to respectively switch the first receiving unit on and off after periods of time measured by the timer. In the communication module, according to an embodiment of the present invention the control unit is adapted to alter the times after which the control unit switches the receiving unit on and off, after reception of a recognition signal, and thus to adapt the activity phases and pauses determined by the timer to those of the patient device. In that way, the electromedical implant, according to an embodiment of the present invention, can easily and efficiently achieve the implementation of a communication connection.

In order to maintain the activity phase of the electromedical implant for longer, as soon as the activity phases of both communication partners have once overlapped, an advantageous embodiment of the electromedical implant is equipped with a first control unit which is adapted to switch off the first receiving unit, after the reception of a recognition signal, only after the elapse of a fourth period of time. That has the advantage that the activity phase of the electromedical implant is not concluded before the activity phase of the patient device, during which the electromedical implant has received the recognition signal, is concluded.

In order to be ready to receive in good time at the beginning of the next activity phase of the patient device and at the same time not to consume any power up to that moment, an embodiment of the electromedical implant provides that the first control unit is adapted to switch on the first receiving unit after reception of a recognition signal communicating the duration of a fifth period of time, after the elapse of the fifth period of time.

A variant embodiment of the electromedical implant has a first control unit which is adapted to cause a predetermined period of time to elapse after reception of a recognition signal, before the first control unit adapts the duration of the activity phase and pause of the receiving unit to the duration of the activity phase and pause of the patient device. In that way, the electromedical implant can place the beginning of its next activity phase at the beginning of the activity phase of the patient device, although only partial overlap of the activity phases of the two communication modules has occurred.

A further embodiment of the electromedical implant has a transmitting unit which is adapted to transmit an acknowledgement signal if the electromedical implant has received a recognition signal from the patient device, by way of its receiving unit. In that way, the electromedical implant can signal to the patient device that temporal matching of the activity phases of the two communication partners has occurred.

In accordance with an embodiment of the present invention, the electromedical implant is a cardiac pacemaker or a defibrillator.

A further aspect of various embodiments of the present invention concerns a patient device comprising a first transmitting unit for transmission in a transmission channel, a second receiving unit and a second control unit connected to a second timer. The second control unit is adapted to switch the first transmitting unit off after the elapse of a sixth period of time and to switch it on after the subsequent elapse of a seventh period of time in periodic alternating relationship. After the reception of an acknowledgement signal, the second control unit switches the first transmitting unit off after the elapse of the sixth period of time and switches it on after the subsequent elapse of an eighth period of time, in periodic alternating relationship. The patient device is thus adapted to adapt the duration of its activity phase and pause to those of the electromedical implant as soon as it received therefrom an acknowledgement signal which indicates temporal overlap of the activity phases of the two communication partners.

In order not to interfere with other communication devices which are transmitting in the same transmission channel, a particular embodiment of the patient device is adapted to check the transmission channel for transmission activity in respect of other communication devices during a ninth period of time which is within the activity pause of the first transmitting unit.

If the transmission channel is occupied by other communication devices, the patient device can save power if it does not switch on the first transmitting unit. Therefore, an advantageous embodiment of the patient device is adapted to set the first transmitting unit in operation after the elapse of its activity pause only when, during the ninth period of time, no transmission activity in respect of other communication devices was found.

In accordance with an embodiment of the present invention, the patient device is adapted in each case once after the elapse of a seventh or eighth period of time in which the patient device has not switched on the first transmitting unit because of transmission activity in respect of other communication devices in the transmission channel, to cause immediately thereafter the elapse of a tenth period of time and to leave the first transmitting unit switched off during the tenth period of time. In that case, the tenth period of time is particularly the duration of an activity phase and an activity pause of the electromedical implant so that the relative displacement of the activity phases of the two communication partners relative to each other is deferred if the transmission channel is occupied. That is advantageous because it prevents the two activity phases missing each other if, during an overlap of the activity phases, the transmission channel is occupied and as a result the two communication partners were unable to establish the overlap of the activity phases.

In an advantageous embodiment of the patient device, the second control unit is adapted to switch off the first transmitting unit, after reception of an acknowledgement signal by the second transmitting unit, only after the elapse of an eleventh period of time. In that case, the eleventh period of time is longer than the sixth period of time. The effect of this is that the patient device prolongs the activity phase of the first transmitting unit for data transmission in the course of a communication connection with the electromedical implant so that more data can be exchanged.

A particularly advantageous embodiment of a patient device is one which, in addition, has a further transmitting and receiving unit and is adapted by way of the additional transmitting and receiving unit to form a wireless data connection and to send data received from the first receiving unit by way of that transmitting unit.

A fourth aspect of an embodiment of the present invention concerns a system including an electromedical implant and a patient device.

A fifth aspect of an embodiment of the present invention concerns a system including an electromedical implant and a patient device.

These and other advantages and novel features of the present invention, as well as details of illustrated embodiments thereof, will be more fully understood from the following description and drawings.

DETAILED DESCRIPTION OF THE INVENTION

Figure 1:
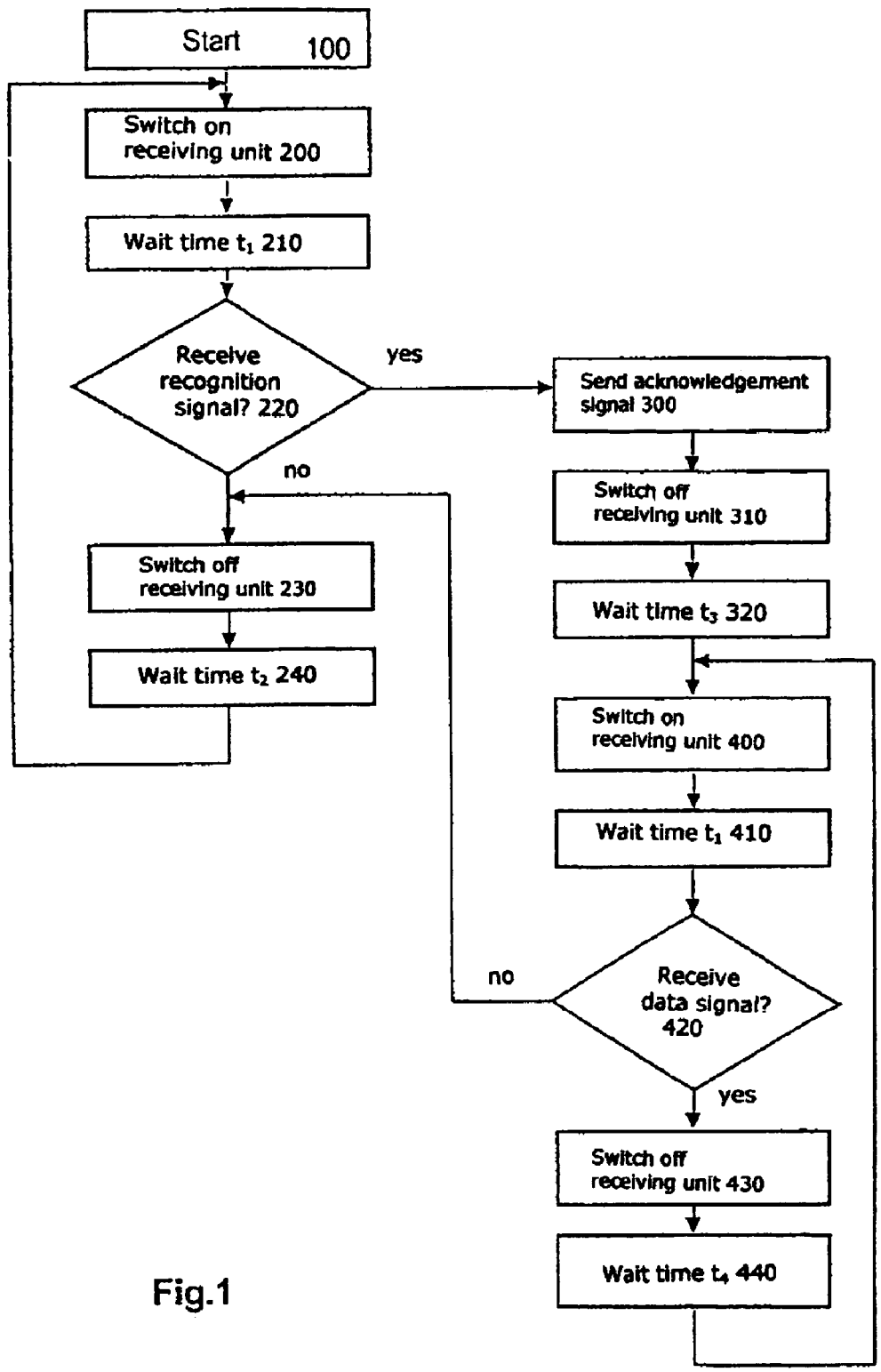
FIG. 1 illustrates a flowchart of an example of a method, in accordance with an embodiment of the present invention.

A variant embodiment, by way of example, of the method according to the present invention for making a wireless communication connection between a patient device and an electromedical implant is shown in FIG. 1. The method begins after the electromedical implant is switched on with the start 100. The method then cyclically runs through the steps 200 through 240 until a branching condition 220 is fulfilled.

In step 200 the receiving unit of the electromedical implant is switched on, whereupon the electromedical implant waits a predetermined time $t_1$ (step 210). During the period $t_1$, the activity phase of the receiving unit, the electromedical implant checks whether a recognition signal in respect of the patient device was received by way of the switched-on receiving unit. After the elapse of the time $t_1$ the method branches at step 220 to the step 230 if no recognition signal was received within the time $t_1$. Otherwise the method branches to the step 300.

If no recognition signal has been received, the receiving unit of the electromedical implant is switched off again in step 230. Then the method waits a second predetermined time $t_2$, the activity pause, (step 240), before returning to the step 200.

If it was found in step 220 that the recognition signal from the patient device was received during the time $t_1$, then in step 300 an acknowledgement signal is sent to the patient device, whereupon the receiving unit is switched off in step 310. Then, in step 320, a time $t_3$ is allowed to elapse, which is so determined that the end of that time coincides with the expected beginning of the next activity phase of the transmitting unit of the patient device. The time $t_3$ may, for example, have been previously communicated to the electromedical implant by the patient device as part of the recognition signal.

Subsequently to the step 320, the steps 400 through 440 are cyclically repeated. In step 400 the receiving unit of the electromedical implant is once again switched on and, during the time $t_1$, transmission and reception of data between the electromedical implant and the patient device are effected as usual (step 410). In step 420 the electromedical implant checks whether, during the period of time $t_1$, it has received data or a recognition signal from the patient device. If that is not the case then synchronization of the activity phases and pauses of the two communication partners has been lost and the method returns to the search mode of steps 200 through 240. If however it was possible to implement data exchange without adverse effect, the receiving unit of the electromedical implant is switched off in step 430. In step 440, a time $t_4$ is allowed to elapse, which corresponds to the duration of the activity pause of the patient device. By the length of the activity pause of the one communication partner being adapted to that of the other communication partner, maximum overlap of the activity phases of the two communication partners is ensured in the next transmission cycle.

Figure 2:
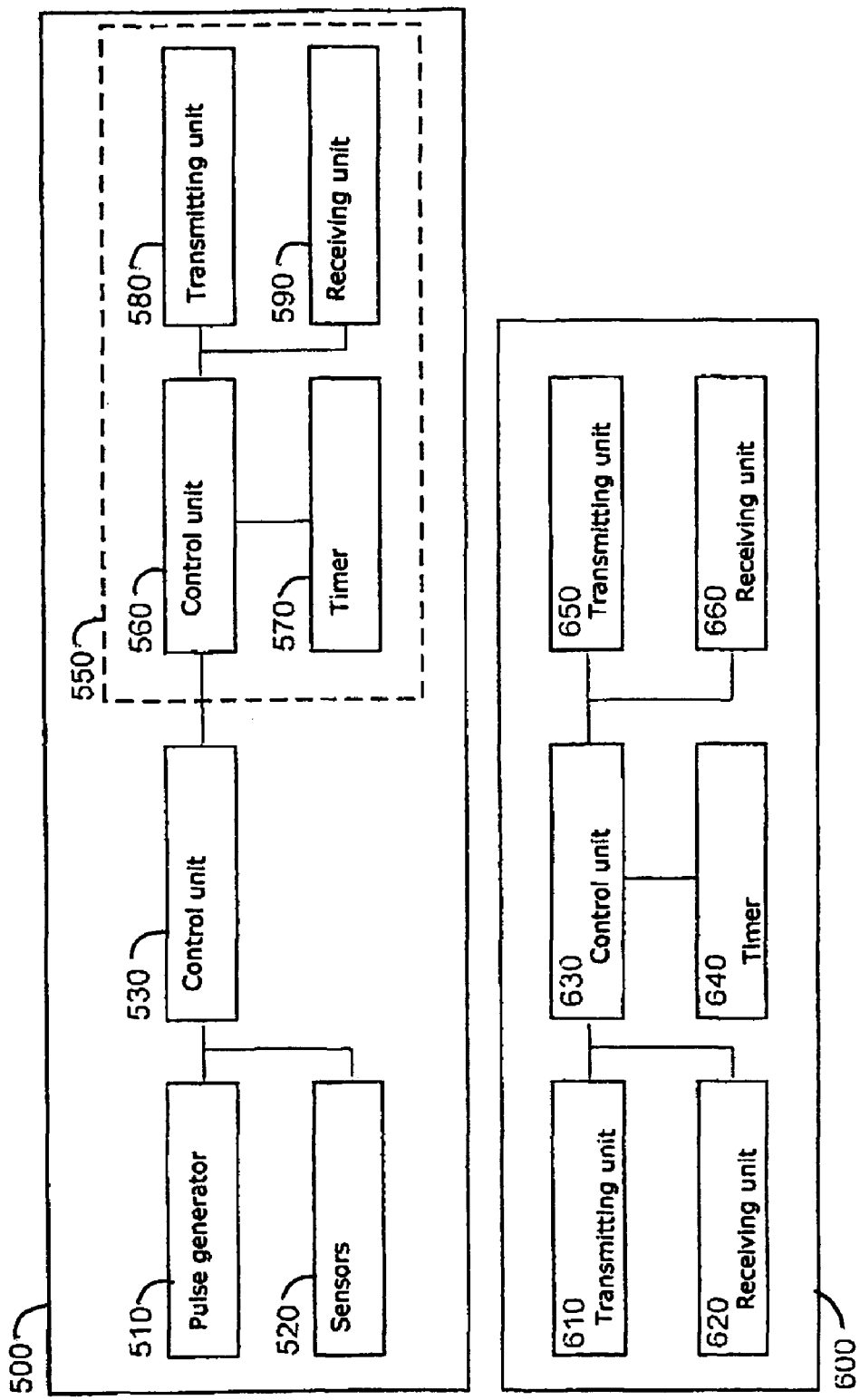
FIG. 2 shows a block diagram of a system including an electromedical implant and a patient device, in accordance with an embodiment of the present invention.

FIG. 2 shows a block diagram of an embodiment of a communication system with an electromedical implant 500 on one side and a patient device 600 on the other side.

The electromedical implant 500 is divided into such blocks which perform medical functions and a communication module 550. The communication module 550 can be seen on the right-hand side of the electromedical implant 500 and is divided into four sub-blocks. Those sub-blocks include the first control unit 560 and the first timer 570 connected thereto, as well as the second transmitting unit 580 and the first receiving unit 590. A pulse generator 510, a block 520 containing medical sensors and a third control unit 530 have been adopted by way of example as medical functional blocks. Those functional blocks may implement the essential functions of a cardiac pacemaker. The third control unit 530 monitors, for example, the heartbeat rate by way of the sensors 520 in such a cardiac pacemaker and, if the heartbeat rate falls below a predetermined value, the third control unit 530 causes the pulse generator 510 to deliver voltage pulses for stimulating the heart.

The blocks 560 through 590 of the communication module 550 are suitable for carrying out the method according to an embodiment of the present invention. In that respect, the first timer 570 determines the times $t_1$ through $t_4$ which, for example, are caused to elapse in the steps 210, 240, 320 and 440. In that respect, the time $t_1$ may correspond to the first period of time, $t_2$ to the second period of time, $t_3$ to the fifth period of time and $t_4$ to the third period of time. The first control unit 560 switches the second transmitting unit 580 and the first receiving unit 590 on or off after times which are determined by the first timer 570. By doing that, it reduces the power consumption of the second transmitting unit 580 and the first receiving unit 590 so that an electromedical implant equipped with such a communication module can remain in the body of a patient longer, with the same battery power.

A system, in accordance with an embodiment of the present invention, includes an electromedical implant 500 and a patient device 600. The first four blocks of the patient device 600, similarly to the four blocks of the communication module 550 of the electromedical implant 500, are the first transmitting unit 610, the second receiving unit 620, the second control unit 630 and the second timer 640 connected thereto. In addition, the patient device also has at least a further, third transmitting unit 650 and a third receiving unit 660. The second control unit 630 switches the first transmitting unit 610 and the second receiving unit 620 on and off after times $t_1$ and $t_4$ determined by the second timer 640. If the two communication partners 500 and 600 are initially not synchronized with each other so that the activity phases of the two devices, during which the transmitting and receiving units 580, 590, 610 and 620 are switched on, do not overlap, then the above-described method, according to an embodiment of the present invention, ensures overlap of the activity phases within a restricted period of time, by virtue of the activity pauses $t_2$ and $t_4$ of the two communication partners being of different lengths. If the patient device 600 receives data from the electromedical implant 500 by way of its first receiving unit 620, it transmits those data to the home monitoring service center by way of the third transmitting unit 650 immediately or upon the next implementation of a communication connection with the home monitoring service center. The third receiving unit 660 is required to make a wireless communication connection with the home monitoring service center, but in a variant of the patient device, according to an embodiment of the present invention, it can also serve to receive data from the home monitoring service center. Those data may be operating parameters and software determining the function of the patient device 600 or operating parameters for the electromedical implant 500, which are transmitted by the patient device 600 by way of the first transmitting unit 610 to the electromedical implant 500.

The patient device 600, which is usually battery-operated, also achieves a longer service life before its batteries have to be charged up by the patient, by virtue of its transmitting and receiving units 610, 620, 650 and 660 being continually switched on and off. By indirectly permitting the communication between the electromedical implant 500 and the home monitoring service center, it considerably reduces the power requirement of the electromedical implant 500.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method of establishing communication between an electromedical implant and an external patient device, said method comprising:

where said implant and said patient device are not initially synchronized with each other for communication, switching between an activity phase and an activity pause of a transmitting unit of said external patient device in periodically alternating relationship;

switching, in periodically alternating relationship, between an activity phase and an activity pause of a receiving unit of said electromedical implant, wherein said activity phase of said transmitting unit of said external patient device is shorter in time duration than said activity pause of the receiving unit of the electromedical implant, ensuring that a relative temporal position of the activity phase of the implant and the activity phase of the external patient device is continually displaced relative to each other such that, within a predetermined maximum time, a temporal overlap occurs between the activity phase of the implant and the activity phase of the external patient device;

said implant receiving a recognition signal from said external patient device during said temporal overlap; and switching off said receiving unit of said implant to enter said activity pause of said receiving unit for a defined period of time in response to receiving said recognition signal.

2. The method of claim 1 further comprising switching from the activity pause of the implant to the activity phase of the implant after the elapse of the defined period of time, wherein the defined period of time indicates to said implant when a next activity phase of said patent device is to start.

3. The method of claim 2 further comprising switching, in periodically alternating relationship, between the activity phase and the activity pause of the receiving unit of the implant, wherein a time duration of the activity pause of the receiving unit of the implant substantially matches a time duration of the activity pause of the patient device.

4. The method of claim 1 wherein said defined period of time is communicated via said recognition signal to said implant.

5. The method of claim 1 wherein said implant sends an acknowledgement signal to said external patient device if said implant has received said recognition signal.

6. The method of claim 5 further comprising adapting a duration of said activity phase and a duration of said activity pause of said patient device to substantially match a duration of said activity phase and a duration of said activity pause of said implant, respectively, upon said patient device receiving said acknowledgement signal.

7. The method of claim 1 wherein said implant is a cardiac pacemaker or a defibrillator.

8. An electromedical implant capable of communicating with an external patient device having an activity phase and an activity pause in periodically alternating relationship said implant comprising:

where said implant and said patient device are not initially synchronized with each other for communication, means for switching, in periodically alternating relationship, between an activity phase and an activity pause of a receiving unit of said electromedical implant, wherein an activity phase of a transmitting unit of said external patient device is shorter in time duration than said activity pause of the receiving unit of the electromedical implant, ensuring that a relative temporal position of the activity phase of the implant and the activity phase of the external patient device is continually displaced relative to each other such that, within a predetermined maximum time, a temporal overlap occurs between the activity phase of the implant and the activity phase of the external patient device;

means for said implant to receive a recognition signal from said external patient device during said temporal overlap; and means for switching off said receiving unit of said implant to enter said activity pause of said receiving unit for a defined period of time in response to receiving said recognition signal.

9. The implant of claim 8 further comprising means for switching from the activity pause of the implant to the activity phase of the implant after the elapse of the defined period of time, wherein the defined period of time indicates to said implant when a next activity phase of said patent device is to start.

10. The implant of claim 9 further comprising means for switching, in periodically alternating relationship, between the activity phase and the activity pause of the receiving unit of the implant, wherein a time duration of the activity pause of the receiving unit of the implant substantially matches a time duration of the activity pause of the patient device.

11. The implant of claim 8 further comprising means for receiving said defined period of time as communicated via said recognition signal to said implant.

12. The implant of claim 8 further comprising means for sending an acknowledgement signal from said implant to said external patient device if said implant has received said recognition signal.

13. The implant of claim 8 wherein said implant is a cardiac pacemaker or a defibrillator.

14. The implant of claim 8 further comprising means for adapting a duration of said activity phase and a duration of said activity pause of said implant to substantially match a duration of said activity phase and a duration of said activity pause of said patient device, respectively.

15. A system, said system comprising:

a patient device having a transmitting unit having at least an activity phase and an activity pause, said transmitting unit capable of transmitting at least one recognition signal; and an electromedical implant having an activity phase and an activity pause, where said implant and said patient device are not initially synchronized with each other for communication, and wherein said electromedical implant includes:

means for switching, in periodically alternating relationship, between said activity phase and said activity pause of a receiving unit of said electromedical implant, wherein said activity phase of said transmitting unit of said external patient device is shorter in time duration than said activity pause of the receiving unit of the electromedical implant, ensuring that a relative temporal position of the activity phase of the implant and the activity phase of the external patient device is continually displaced relative to each other such that, within a predetermined maximum time, a temporal overlap occurs between the activity phase of the implant and the activity phase of the external patient device;

means for said implant to receive said at least one recognition signal from said external patient device during said temporal overlap; and means for switching off said receiving unit of said implant to enter said activity pause of said receiving unit for a defined period of time after receiving said at least one recognition signal.

16. A system, said system comprising:

a patient device having a transmitting unit providing at least an activity phase and an activity pause, said transmitting unit capable of transmitting at least one recognition signal; and an electromedical implant providing an activity phase and an activity pause, where said implant and said patient device are not initially synchronized with each other for communication, and wherein said electromedical implant includes:

means for switching, in periodically alternating relationship, between said activity phase and said activity pause of a receiving unit of said electromedical implant, wherein said activity phase of said transmitting unit of said external patient device is shorter in time duration than said activity pause of the receiving unit of the electromedical implant, ensuring that a relative temporal position of the activity phase of the implant and the activity phase of the external patient device is continually displaced relative to each other such that, within a predetermined maximum time, a temporal overlap occurs between the activity phase of the implant and the activity phase of the external patient device, means for said implant to receive said at least one recognition signal from said external patient device during said temporal overlap, means for switching off said receiving unit of said implant to enter said activity pause of said receiving unit for a defined period of time after receiving said at least one recognition signal, means for switching from the activity pause of the implant to the activity phase of the implant after the elapse of the defined period of time, wherein the defined period of time indicates to said implant when a next activity phase of said patient device is to start and, means for switching, in periodically alternating relationship, between the activity phase and the activity pause of the receiving unit of the implant, wherein a time duration of the activity pause of the receiving unit of the implant substantially matches a time duration of the activity pause of the patient device, wherein said electromedical implant is a cardiac pacemaker or a defibrillator.

* * * * *